United States Patent

Flamant et al.

[11] Patent Number: 6,126,588
[45] Date of Patent: *Oct. 3, 2000

[54] FLEXIBLE MAGNETIC PAD

[75] Inventors: Hubert F. Flamant, Dallas; Johannes Spijkerman, Arlington; Ivan H. Darius, Richardson, all of Tex.

[73] Assignee: MTI, Inc., Dallas, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/526,751

[22] Filed: Sep. 11, 1995

Related U.S. Application Data

[63] Continuation of application No. 08/167,673, Dec. 15, 1993, abandoned.

[51] Int. Cl.[7] .................................... A61N 1/00
[52] U.S. Cl. ............................................ 600/15
[58] Field of Search .............................. 600/9–15

[56] References Cited

U.S. PATENT DOCUMENTS

| | | | |
|---|---|---|---|
| 3,943,912 | 3/1976 | Nakayama | 600/15 |
| 4,022,189 | 5/1977 | Boxer | 600/15 |
| 4,489,711 | 12/1984 | Latzke | 600/15 |
| 4,549,532 | 10/1985 | Baermann | 600/15 |
| 4,587,956 | 5/1986 | Griffin et al. | 600/15 |

FOREIGN PATENT DOCUMENTS

| | | | |
|---|---|---|---|
| 3333083 | 4/1985 | Germany | 600/15 |

*Primary Examiner*—Samuel G. Gilbert
*Attorney, Agent, or Firm*—Slater & Matsil, L.L.P.

[57] ABSTRACT

A flexible magnetic pad for therapeutic use having single pole magnetic surfaces includes a mixture of a flexible synthetic material and magnetic particles having a high magnetic retentivity with a residual induction of at least 0.8 Tesla. Preferably, the synthetic material is silicone rubber and the magnetic particles are Neodymium-Iron-Boron. Sealing layers of flexible synthetic material surround the mixture to prevent disengagement of the particles. The pad is form-fitting to the contours of the body and has an elasticity enabling 200% elongation.

12 Claims, 1 Drawing Sheet

FLEXIBLE MAGNETIC PAD

This is a continuation of application Ser. No. 08/167,673 filed on Dec. 15, 1993 now abandoned.

TECHNICAL FIELD

The present invention relates generally to the therapeutic use of magnetic fields, and specifically, to a magnetic pad having enhanced flexibility for enabling the pad to form-fit to the contours of the human body and having single pole surfaces for increasing magnetic penetration and blood flow within the treatment area.

BACKGROUND OF THE INVENTION

It has been known for quite some time that magnetic fields, such as those created by permanent magnets, can have a therapeutic effect on the human body. These therapeutic effects are caused by increased blood circulation in the area of the body under the influence of the magnetic field. Thus to be effective, the magnetic field must extend throughout the portion of the body being treated.

Magnetic pads, however, have had limited utility as therapeutic devices due to their rigidity and their resultant inability to deliver magnetic fields throughout the entire portion of the body being treated. In particular, magnetic pads have had limited flexibility due to their construction from rigid permanent magnets or due to the high percentage of magnetic material suspended within the pads which, while still allowing the pads to bend, has not allowed them to conform to the contours of the treatment area, especially where the treatment area consists of a small appendage such as a finger or a joint such as an elbow or shoulder.

Additionally, the effectiveness of known magnetic pads has been limited by the alternating orientation of the magnetic poles found on most magnetic pads. There has been much effort expended in creating magnetic pads having an alternating magnetic pole orientation of optimal design to supposedly induce electrical currents within the treatment area irrespective of the orientation of the blood vessels. As an example, magnetic pads have been developed with alternating magnetic poles arranged in spirals, checkerboard patterns, rings, radial sectors, etc.

While these alternating magnetic pole designs are more effective at inducing electrical currents within the treatment area, they have several drawbacks. First, magnetic field strength decreases much more rapidly per unit distance from a magnetic pad having alternating magnetic poles than one having single pole sides. Thus, the magnetic fields of the alternating magnetic pole pads fail to penetrate as deeply into the treatment area and are often only responsible for surface effects. To increase penetration depth, stronger magnets need to be used or additional percentages of magnetic material must be suspended within the pad, thereby further increasing the rigidity of the magnetic pad as discussed above.

In addition, alternating magnetic pole designs do not maximize the Lorentz forces experienced by the charged particles within the blood vessels. Under the influence of a directionally changing magnetic field, the charged particles within the treatment area will first be accelerated, but then slowed as they travel into the adjacent magnetic field because the Lorentz force experienced by the particles reverses. This stop and go action prevents optimal enhancement of blood flow through the vessels.

What is needed is a magnetic pad capable of conforming to the contours of the human body to enlarge the area under the influence of the magnetic field, as well as to enable magnetic pads to form-fit around small appendages and joints. In addition, such a magnetic pad should have single pole magnetic surfaces to improve field penetration and blood flow within the treatment area.

SUMMARY OF THE INVENTION

The foregoing problems are solved and a technical advance is achieved by a magnetic pad that comprises magnetic particles having a residual induction over 0.8 T cured within a flexible synthetic material, which pad is magnetized to have single poles on each surface.

In an illustrative embodiment, the magnetic pad comprises an approximately 1.5 mm thick core layer of a flexible synthetic material, preferably silicone rubber, embedded in which are particles of a ferromagnetic material that can be easily magnetized in a preferred direction. The particles must have a high magnetic retentivity with a residual induction of over 0.8 T to produce the desired magnetic remanent field while retaining the flexibility and elasticity of the synthetic material. Surrounding the core layer are 25 to 75 micron thick sealing layers of a flexible synthetic material, also preferably silicone rubber.

The core layer of the magnetic pad is formed by airless mixing the magnetic particles in the silicone rubber material, together with a curing retardant to prevent immediate, undesired curing. The resulting mass is formed into sheets, preferably 1.5 mm thick, either through calendering or a continuous casting process or is poured into appropriately dimensioned molds. After curing, the core layer is cut into sizes of differing dimensions dependent upon the area of desired treatment. Once cut, the core layer is surrounded by the sealing layers through coating. Finally, the magnetic pad is magnetized by introducing the pad into the airgap of an electromagnet in a known manner to cause one side of the pad to be a north pole and the opposite side of the pad to be a south pole.

The invention results in several technical advantages. Generally, the invention increases the therapeutic ability of magnetic pads by providing a form-fitting device having single magnetic poles on each surface.

A further technical advantage is the increased penetration depth of the pad's magnetic field to reach more of the treatment area.

A further technical advantage is the maximization of the Lorentz force effects experienced within the treatment area.

A further technical advantage is the ability to conform the magnetic pad around elbows and other curved body parts.

A further technical advantage is the ability to wrap the magnetic pad around even the smallest human extremities and cylindrical body parts.

A further technical advantage is that the magnetic pad of the present invention is not restrictive enabling its use during exercising or other movement.

A further technical advantage is that joints in the treatment area need not be immobilized during treatment.

A further technical advantage is the ability to use the magnetic pad for all parts of the body, thereby eliminating the need for a variety of pads for different body parts.

BRIEF DESCRIPTION OF THE DRAWINGS

The above brief description, as well as further objects, features and advantages of the present invention will be more fully appreciated by reference to the following detailed description of the presently preferred but nonetheless illustrative embodiments in accordance with the present invention when taken in conjunction with the accompanying drawings wherein.

DESCRIPTION OF THE PREFERRED EMBODIMENTS

Figure 1:
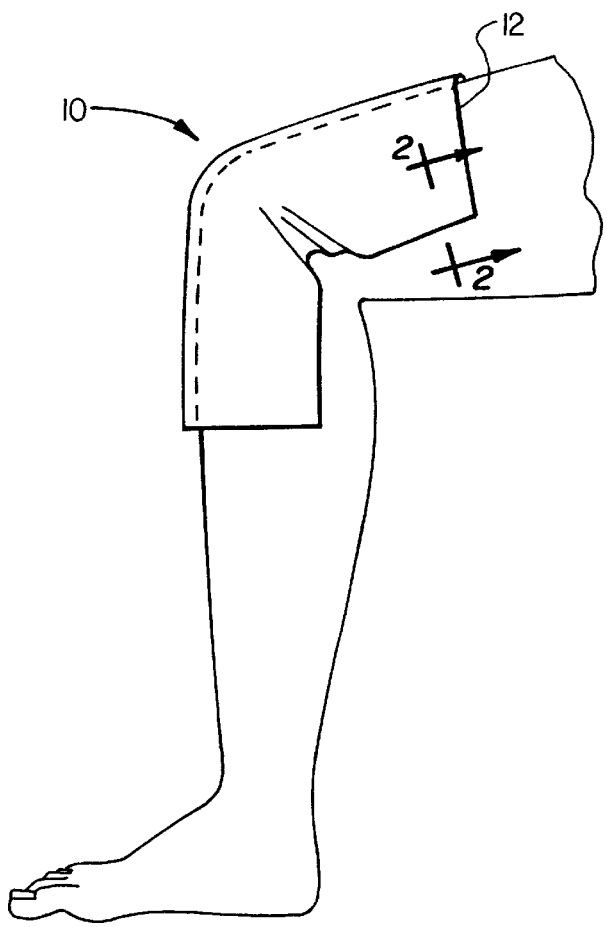
FIG. 1 is an elevation view of the invention draped over a body portion.

In FIG. 1, the reference numeral 10 designates a magnetic pad embodying features of the present invention. The magnetic pad 10 is used in connection with a body member 12 for providing relief from various pains and disorders. As shown in FIG. 1 and as described below, the magnetic pad 10 is formed to be flaccid to enable it to drape over and fit any contour of the human body, such as the knee area as shown, or to even to wrap around a single finger. The magnetic pad is also highly elastic and experiences over 200% elongation enabling it to give when wrapped around joints.

Figure 2:
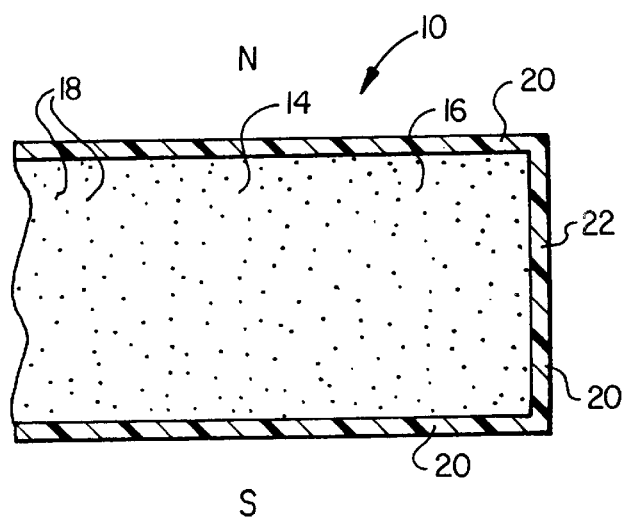
FIG. 2 is a fragmentary sectional view taken along the line 2—2 of FIG. 1.

Referring to FIG. 2, one embodiment of the magnetic pad 10 is shown formed of a core layer 14 of a flexible synthetic material 16, embedded in which are particles 18 of a ferromagnetic material that can be easily magnetized in a preferred direction. Sealing layers 20 of a flexible synthetic material 22 surround the core layer 14 to prevent any of the particles 18 from disengaging. The core layer is preferably 1.25 to 6.25 mm in thickness, and most preferably has a thickness of approximately 1.5 mm. The sealing layers 20 are preferably only 25 to 75 microns thick.

The materials 16 and 22 must be compatible with human skin (i.e., hypo-allergenic) and enable the magnetic pad 10 to be conformable to the body surface to be treated, and in a preferred embodiment are one or two part silicon rubber. Silicone rubber also provides the magnetic pad 10 with desired chemical and temporal stability, as well as with the substantial elongation described above.

To maintain the flexibility, elasticity and conformability of the magnetic pad 10, the amount of the particles 18 embedded in the core layer 14 must be limited, thereby requiring the particles 18 to have a high magnetic retentivity with a residual induction of over 0.8 T (making ferrites inutile) to produce the desired magnetic remanent field necessary to provide therapeutic relief as described below. The size of the particles 18 can generally range between 50 and 350 microns, so long as they are large enough to act as permanent magnets and small enough to fit within the core layer 14. In a preferred embodiment, the particles 18 are 200 micron Neodymium-Iron-Boron ($Nd_2Fe_{14}B$) particles such as those comprising Magnequench's MQP-B powder that have a residual inductance of 0.8–0.84 T.

Preferably, the core layer 14 of the magnetic pad 10 is formed by airless mixing 40–60% by weight of the Neodymium-Iron-Boron particles 18, but most preferably 50%, in the one or two part silicone rubber material 16, together with a peroxide or platinum curing retardant to prevent immediate, undesired curing. The resulting mass is then formed into sheets, preferably 1.5 mm thick as described above, either through calendering or a continuous casting process or is poured into appropriately dimensioned molds. Backing sheets, such as Mylar sheeting material, may be utilized as is known in the art to provide a nonadherent surface for maintaining the desired thickness of the core layer 14 through the curing process. Depending upon the forming process, the core layer 14 is either platinum or peroxide cured, with the continuous casting platinum 120–150° C. dry heat cure being preferred over the steam peroxide cures used with calendering and molding.

After curing, the core layer 14 is cut into sizes desired for applying the magnetic pad 10 to the body. Typically, the core layer 14 will be cut into either circular or rectangular patterns of differing dimensions dependent upon the area of desired treatment, but it is understood that the magnetic pad 10 could be cut to any size for custom applications.

Once cut, the core layer 14 is surrounded by the approximately 25 to 75 micron thick sealing layers 20 by coating the core layer 14 with the silicone rubber material 22 to effectively trap the particles 18. The magnetic pad 10 is then introduced into the airgap of an electromagnet capable of producing a magnetic flux density in excess of 2.5 T to impart a magnetic remanent field to the particles 18. When the particles 18 are Neodymium-Iron-Boron, the resulting magnetic field measured at 6.35 mm from the magnetic pad 10 will exceed 2 mT, it being understood that increased percentages of particles 18 will result in higher remanent fields. As shown in FIG. 2, the magnetic pad 10 is magnetized in a known manner to cause one side of the pad to be a north pole and the opposite side of the pad to be a south pole, thereby avoiding the alternating magnetic poles so prevalent in the prior art.

In use, the magnetic pad 10 is placed on a portion of the body needing treatment and secured in place by elastic bands, bandages, band-aids or in other known ways (not shown), with the south pole side of the magnetic pad 10 preferably being placed closest to the body. An adhesive strip can also be attached to the magnetic pad 10 to facilitate securing the pad to the treatment area. Due to the flexibility of the magnetic pad 10, the pad will conform to the treatment area regardless of the size or angular orientation of the body part. The magnetic field generated by the magnetic pad 10 penetrates into the body and imparts a Lorentz force on the numerous charged particles flowing within the blood vessels causing increased blood flow through the treatment area.

Several technical advantages result from the foregoing. Generally, the magnetic pad 10 increases the therapeutic ability of magnetic fields by providing a form-fitting device having single magnetic poles on each surface. For example, providing a single pole magnetic device increases the penetration of the magnetic field into the treatment area as compared to alternating magnetic pole pads of equal magnetic strength as measured at their respective surfaces. Moreover, the single pole field maximizes the Lorentz forces experienced within the treatment area. Under a directionally changing magnetic field, the Lorentz forces would alternate as well, thereby causing the charged particles within the body to be pushed in one direction and then be suddenly slowed and pushed in the opposite direction as the particles move through the field.

The increased flexibility of the magnetic pad 10 provides additional technical advantages. By being form-fitting, the magnetic pad 10 provides magnetic field penetration over a greater percentage of the treatment area as it can be conformed around elbows and other curved body parts. Thus in treating a sore shoulder, the magnetic pad 10 will lie smoothly against the front, top and back of the shoulder, as well as along the neck and upper arm, thereby penetrating the entire area. The magnetic pad 10 can also be used for even the smallest human extremities and cylindrical body parts such as fingers and ankles. In addition, such joints do not have to be immobilized during treatment as the magnetic pad 10 is highly elastic. In fact, the magnetic pad 10 is non-restrictive in general enabling its use during exercising or other movement. Further, specially configured magnetic pads are not necessary for each differently shaped treatment area as the flexibility of the magnetic pad 10 allows it to form-fit to all contours of the human body.

It is also understood that variations may be made in the present invention without departing from the spirit and scope of the invention. For example, the particles 18 need not be Neodymium-Iron-Boron particles, so long as they provide a residual induction of over 0.8 T. Further, those skilled in the art will recognize that the percentage of particles 18 required in the core layer 14 can be reduced as the particles' residual induction increases. By further decreasing such percentage, the flexibility of the magnetic pad 10 can be further increased. Moreover, besides being cut into the shapes described above, the magnetic pad 10 can be cut into specially designed shapes, such as to fit within a shoe.

Although illustrative embodiments of the present invention have been shown and described, a wide range of modification, change and substitution is intended in the foregoing disclosure, and in certain instances some features of the invention may be employed without a corresponding use of other features. Accordingly, it is appropriate that the appended claims be construed broadly and in a manner consistent with the scope of the invention.

What is claimed is:

1. A magnetic pad for therapeutic use, comprising:
   a stretchable sheet readily conformable to human joint-like structures for enveloping same, comprising a single magnet, said single magnet comprising a mixture of synthetic material and magnetic particles, wherein said particles comprise Neodymium-Iron-Boron particles between 50 and 350 microns and comprise 40–60% by weight of said sheet.

2. The magnetic pad of claim 1 further comprising a synthetic material surrounding said sheet to prevent disengagement of said particles from said sheet.

3. The magnetic pad of claim 1 wherein said particles have a high magnetic retentivity with a residual induction of at least 0.8 Tesla.

4. The magnetic pad of claim 1 wherein said particles are Neodymium-Iron-Boron.

5. The magnetic pad of claim 1 wherein each side of said sheet exhibits a single magnetic pole.

6. The magnetic pad of claim 1 wherein said synthetic material is silicon rubber.

7. The magnetic pad of claim 1 wherein said sheet is elastic.

8. The magnetic pad of claim 1 wherein said sheet has an elasticity enabling 200% elongation.

9. The magnetic pad of claim 1 wherein said magnetic particles are about 200 microns.

10. A method of providing therapeutic relief to a person, comprising the steps of draping over an intended treatment area of the person a magnetic pad comprising a single magnet and having single pole magnetic south and magnetic north sides, said magnetic pad being comprised of a synthetic material and magnetic particles embedded therein, wherein said magnetic particles comprise Neodymium-Iron-Boron particles between 50 and 350 microns and comprise 40–60% by weight of said pad and wrapping the magnetic pad over the treatment area to form-fit over the contours of the treatment area in a non-restrictive manner.

11. The method of claim 10 wherein said magnetic particles are about 200 microns.

12. A magnetic pad for therapeutic use, comprising a stretchable, elastic medium in which is embedded magnetic particles having a concentration of 40–60% by weight magnetic particles and magnetic particles having a retentivity of at least 0.8 Tesla.

* * * * *